Figure 7:
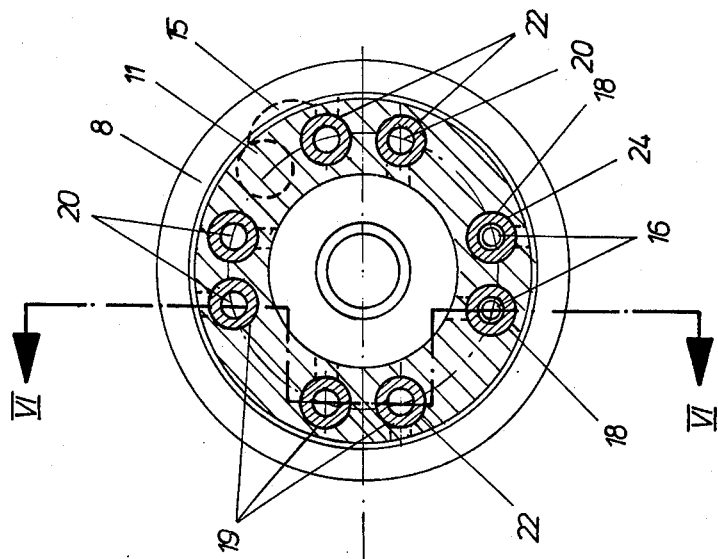

United States Patent [19]

Reich et al.

[11] 4,213,756
[45] Jul. 22, 1980

[54] DENTAL-INSTRUMENT HANDLE

[75] Inventors: Heinrich Reich, Hochdorf; Eugen Eibofner, Biberach, both of Fed. Rep. of Germany

[73] Assignee: Kaltenbach & Voigt GmbH & Co., Biberach, Fed. Rep. of Germany

[21] Appl. No.: 941,841

[22] Filed: Sep. 12, 1978

[30] Foreign Application Priority Data

Sep. 13, 1977 [DE] Fed. Rep. of Germany ....... 2741148

[51] Int. Cl.² ........................... A61C 1/08; A61C 1/12
[52] U.S. Cl. ....................................... 433/126; 433/82
[58] Field of Search ............... 285/277, 137 R; 32/26, 32/27

[56] References Cited

U.S. PATENT DOCUMENTS

| | | | |
|---|---|---|---|
| 3,229,656 | 1/1966 | Bodey | 285/137 R |
| 3,252,719 | 5/1966 | Borden | 285/137 R |
| 3,423,110 | 1/1969 | Hansen et al. | 285/277 |

*Primary Examiner*—Robert Peshock
*Attorney, Agent, or Firm*—Haseltine, Lake & Waters

[57] ABSTRACT

A dental handpiece in which an elongated handle sleeve is transversely divided by formation of an anterior sleeve showing a receptacle for a drivable dental-treatment instrument. A connected grip sleeve is detachable by a rotatable tightening ring. The handle sleeve has a coolant line running at least in the area of the transverse space within the inside of the sleeve outside the longitudinal axis of the handle sleeve, the coolant line is also transversely divided and leads to the area of the dental-treatment instrument. Two front sides of the anterior sleeve and the grip sleeve have both two front sides facing each other. One front side is provided with a projecting connecting piece for the cooling line and the other front side is provided with a connecting socket for an insertable connecting piece. The front side of the grip sleeve is provided with guide pins projecting from it and forming a catch device opposing pin sockets of elastic material and serving as an opposing catch device to accept the guide pins. The connecting pieces of each coolant line are connected with a belt canal from which the cooling line portion of the anterior sleeve leads to the area of the dental-treatment instrument.

5 Claims, 10 Drawing Figures

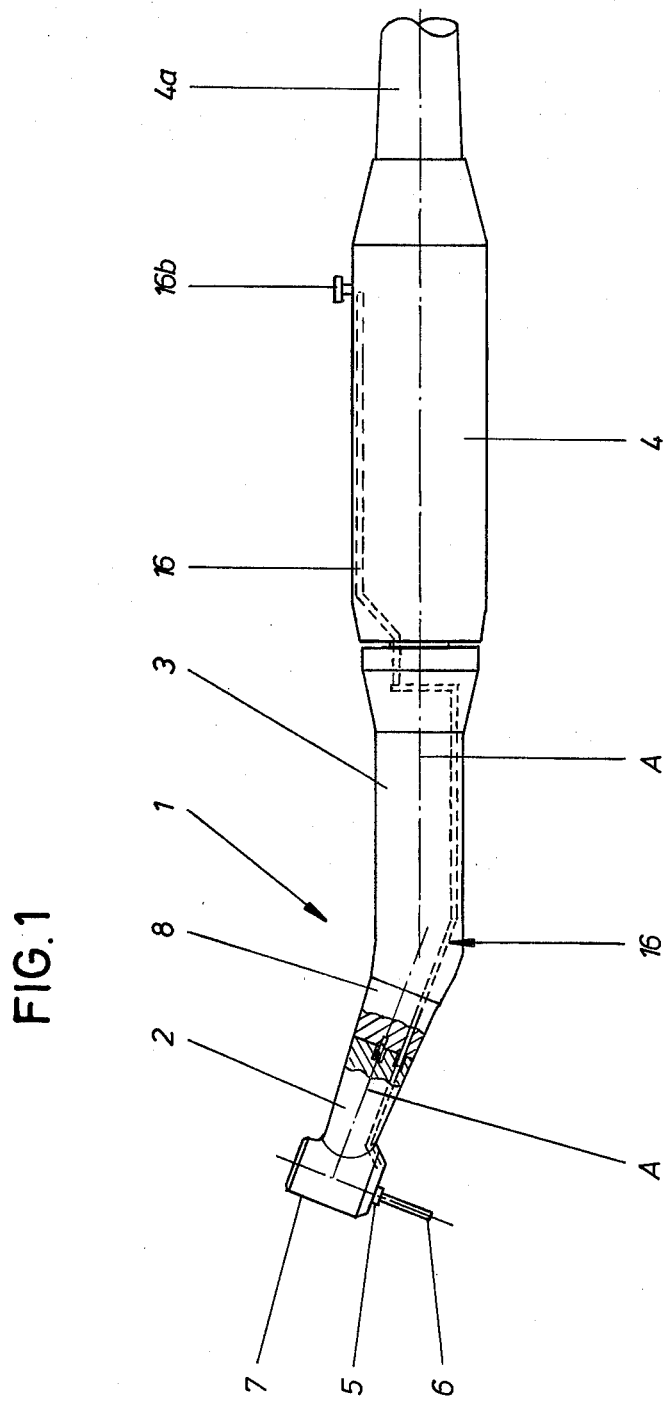

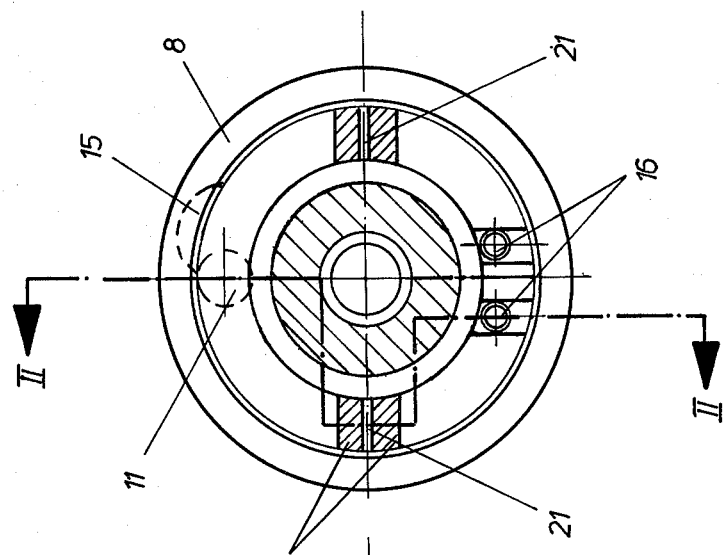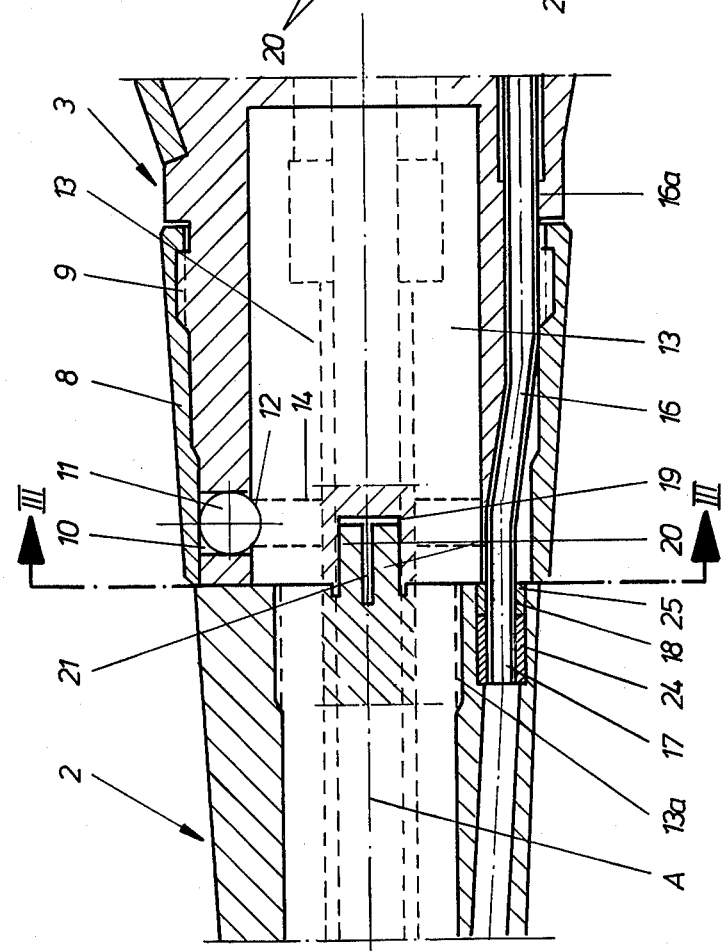

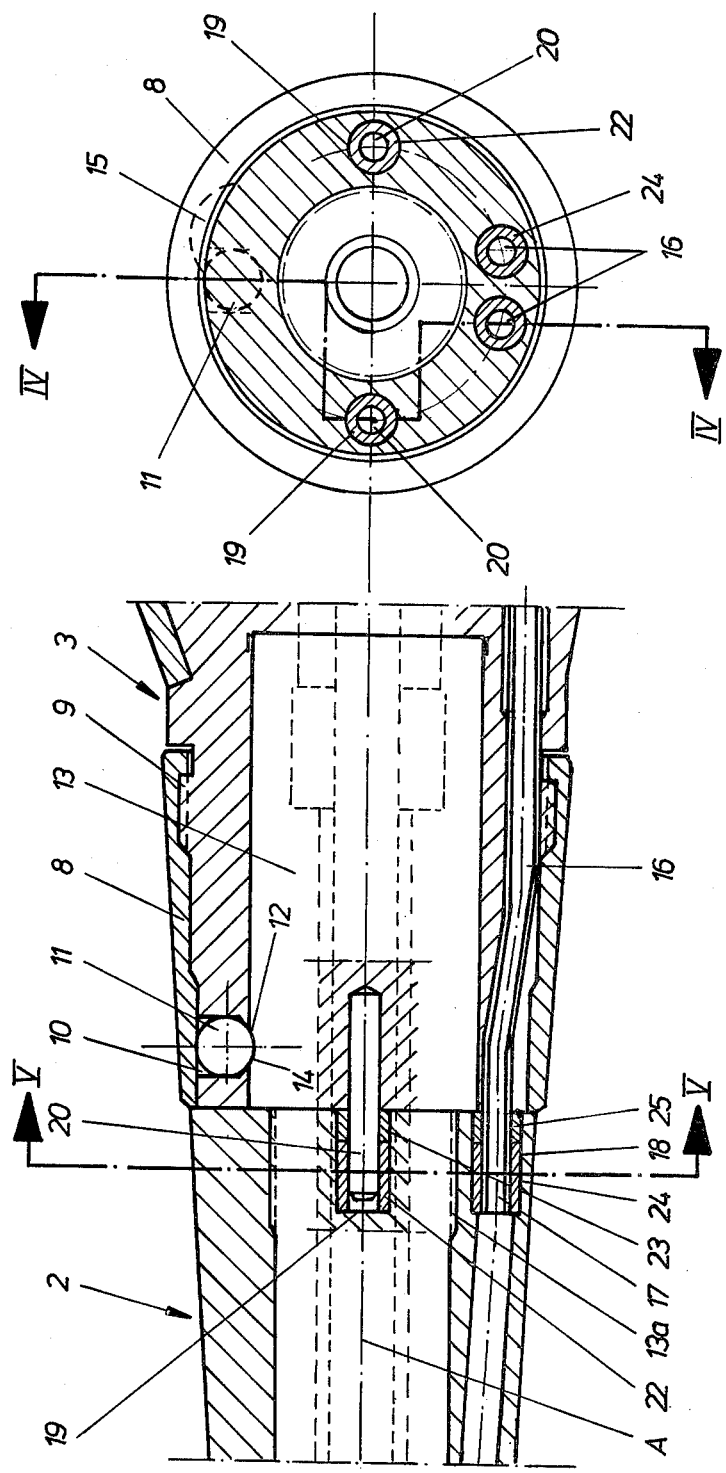

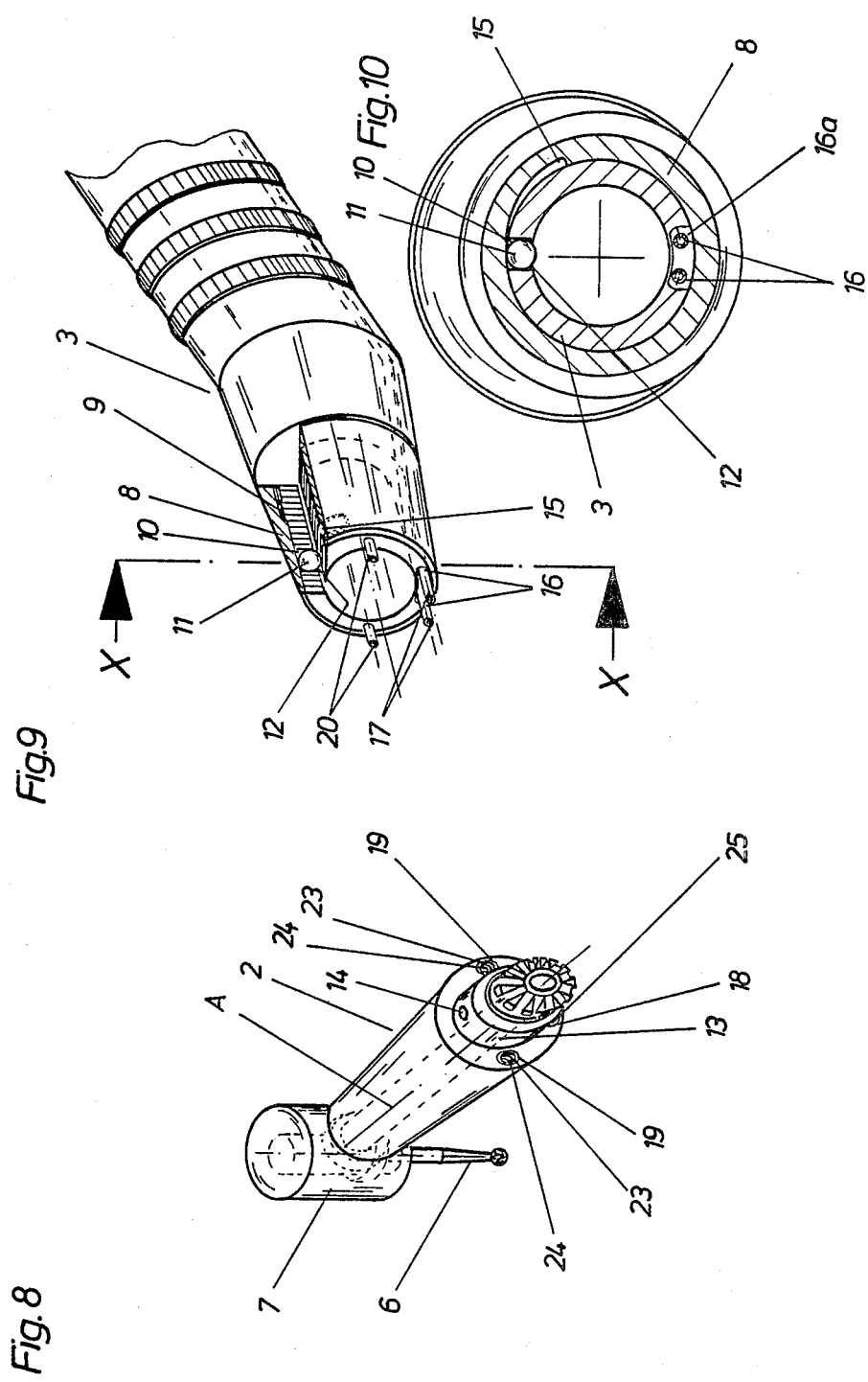

DENTAL-INSTRUMENT HANDLE

The present invention concerns a dental-instrument handle, consisting of an elongated handle sleeve, that is transversely divided by formation of an anterior sleeve showing a receptacle for a rotating dental-treatment drill and a connected grip sleeve detachable by means of a twistable tightening-ring; wherein, the handle sleeve has a coolant line running at least in the area of the transverse space within the inside of the sleeve outside of the longitudinal axis of the handle sleeve and leading diagonally to the area of the dental-treatment drill; wherein, of the two front sides of the anterior sleeve and the grip sleeve, both facing one another, the one front side is provided with a main connecting piece of the coolant line and the other front side is provided with a connecting socket for the insertable connecting piece.

A dental-instrument handle of this type is known by DT-PS 11 16 860. By tightening the tightening-ring, the connecting piece inserted in the connecting socket and perhaps even the connecting socket would break down as a consequence of the lateral or radial force of the moment of rotation exerted by the turning of the tightening-ring, which leads to the buckling or breaking of the attached parts, that is, the connecting piece and/or the connecting socket.

The object of the present invention is to create a dental-instrument handle of the above-mentioned variety, in which the connecting piece and/or the connecting socket are protected against lateral and/or radial forces.

It is a particular object of this invention, that in a handle of the above-mentioned variety, both front sides facing one another are provided with flexible catch means and —with respect to the axis of the handle—axially engageable in opposing The proposed catch means and opposing catch means offer sufficient opposition to the moment of rotation, by turning of the tightening-ring, so that an opposing turning by the anterior sleeve and grip sleeve is prevented and that no lateral force can be exerted on the connecting piece and/or the connecting socket of the coolant line. By means of the flexible meshing of the catch- and opposing catch means, the latter operate like grip-spring tensioning elements, that, by attainment of a compensation for play, a good bridging of allowable variations is effected as well as the catch- and opposing catch elements, also the connecting piece and the connecting socket.

A further dental-instrument handle is known in GB-PS 22 552 A.D. 1907 having catch means and opposing catch means axially engageable in one another, ordered on the both front sides facing one another of the anterior sleeve and the grip sleeve, as such with a tightening-ring for the detachable connecting of the anterior sleeve and the grip sleeve; however, the handle sleeve has no coolant line and the catch means and opposing catch means do not engage flexibly in one another. As an exact fit cannot be produced in manufacturing—this entails a gripping of the catch means and opposing catch means not free of play, which leads to a undesired radial rocking motion between the anterior sleeve and grip sleeve. By transferring this well known arrangement to a handle as in DT-PS 11 16860 additional undesired radial forces would be exerted on the connecting piece and/or the connecting socket of the coolant line by the turning of the tightening-ring. This would be prevented by the flexibly engaging catch means and opposing catch means that operate as grip-spring tensioning elements according to the invention.

The catch means is provided on one of the two front sides and the opposing catch means on the other front side.

Insofar as many catch means as well as many opposing catch means are provided at any time, and the catch means as well as the opposing catch means are arranged symmetrically on a circular path, it is particularly easy to insert the catch means and opposing catch means into one another.

The connecting piece and/or the connecting socket of one coolant line are also arranged on the circular path of the catch means and the opposing catch means.

Insofar as the characteristic is added hereto, that the connecting piece(s) and the connecting socket(s) of principally two coolant lines are arranged symmetrically on the circular path together with the catch means and/or opposing catch means, the anterior sleeve and the grip sleeve separated from this can be connected to each other in various reciprocal turning positions by engaging together the connecting piece and/or catch means into the corresponding connecting socket and/or opposing catch means. Six catch means with corresponding opposing catch means are provided hereto, and coolant lines with a connecting piece and a connecting socket.

At least the one coolant line with connecting piece and connecting socket as well as the catch means and opposing catch means are arranged chiefly in the wall of the anterior sleeve and/or the wall of the grip sleeve. Thereby, the coolant line, in order to facilitate its cleaning and/or dismantling, can be arranged in special canals, that are provided in the walls of said sleeves.

A particular embodiment of the invention is characterized in that, for formation of the catch means the one front side is provided with at least one group of clamping jaws aranged next to one another, left alone as one slot effecting the flexible gripping, and for formation of the opposing catch means the other front side is provided with at least one recess that receives together all clamping jaws of a group.

A further embodiment of the invention provides that, for the formation of the catch means the one front side has at least one guide pin and for formation of the opposing catch means the other front side has at least one plug socket to receive the guide pin, that has elastic middles on its insides on the guide pin as a supplement. The connecting socket of at least one coolant line also has, on its inside on the insertable connecting piece, elastic middles. The elastic middles have a Shore-hardness of 70° to 80°.

A further improvement of the various possible turning positions between the anterior sleeve and grip sleeve, provides that the guide pin as well as the connecting piece of at least one coolant line are arranged symmetrically on a circular path on the front side of the grip sleeve, and the plug sockets as well as the connecting socket of at least one coolant line are arranged symmetrically on a circular path, having the same diameter as the first-mentioned circular path, on the front side of the anterior sleeve, wherein the plug sockets are connected with a belt canal, from there the coolant line portion of the anterior sleeve leads to the area of the dental-treatment drill.

Various embodiments of the invention are shown in the accompanying drawings.

Figure 6:
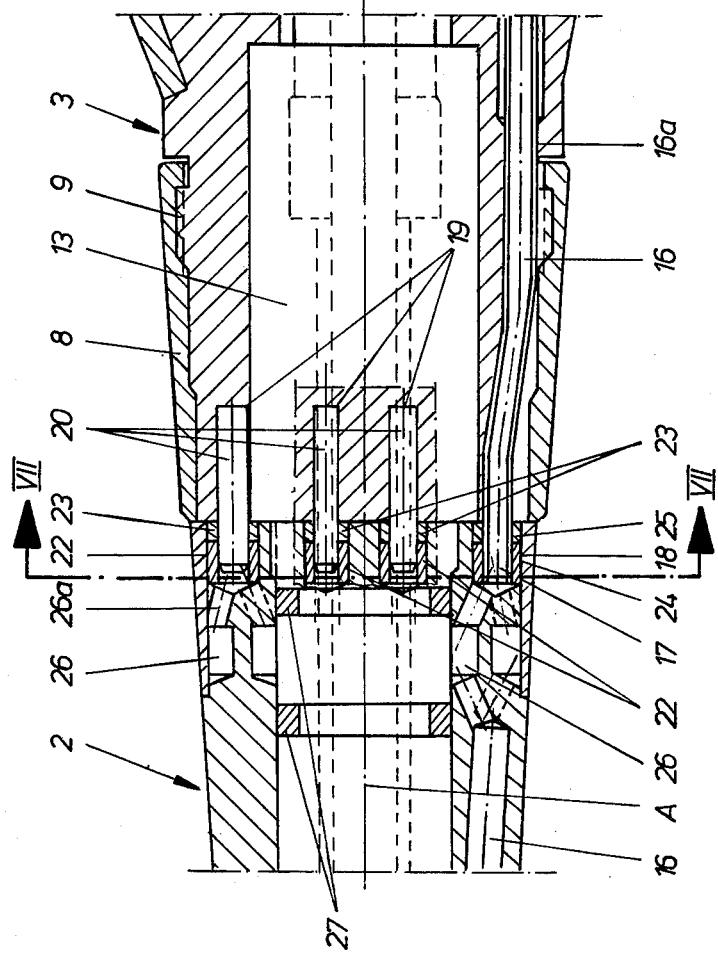

As shown:

FIG. 1 is a dental-instrument handle in a side view,

FIG. 2 is the area of the transverse division of the handle in an enlarged scale in section along the line II—III in FIG. 3, FIG. 3 is a section along the line III—III in FIG. 2, FIG. 4 is a changed form in comparison to FIG. 2 in section along line IV—IV in FIG. 5, FIG. 5 is a section along line V—V in FIG. 4, FIG. 6 is a changed form in comparison to FIG. 4 in section along line VI—VI in FIG. 7 and FIG. 7 is a section along line VII—VII in FIG. 6.

FIG. 8 is a perspective view of the anterior sleeve of the handle towards the side facing the grip sleeve, FIG. 9 is a perspective view of the grip sleeve of the handle towards the side facing the anterior sleeve, and FIG. 10 is a section through the line X—X in FIG. 9 in the area of the indentation 15.

The dental-instrument handle shown in FIG. 1 consists of an elongated handle sleeve 1, that is transversely divided by formation of an anterior sleeve 2 and a grip sleeve 3. A connecting sleeve 4 is added onto the grip sleeve 3 of the handle sleeve 1 in an appropriate and well know way, that can be turned in opposition to the handle sleeve 1. The anterior sleeve 2 shows a receptacle 5, for example, a collet, for a rotatable dental-treatment drill 6. The operation of the dental-treatment drill 6 can be effected by means of an air turbine (not shown) built into the head of the handle 7, by an air motor (not shown) or by a vertical capstan stored in the handle sleeve 1 (also not shown). In the last case the vertical capstan can be set in motion by the drive-connector of a electric motor (not shown) arranged in the connecting sleeve 4. 4a designates a flexible energy supply lead.

A twistable tightening-ring 8 is arranged on the grip sleeve 3 by means of a screwable coil 9. Beneath the tightening-ring 8 in an open work 10 is a clamp ball bearing 11, that is held in by means of a base opening 12 of the open work 10 which is smaller in diameter. For locking with the anterior sleeve 2, the clamp ball bearing 11 engages in a cavity 14 that is worked into the outer surface of a cylindrical extension 13 of the anterior sleeve 2, that is in the form of an annular tee-slot as indicated in the case in FIG. 2. The extension 13 is screwed to the anterior sleeve 2 by means of a coil 13a. In the inner wall of the tightening-ring 8 an indentation 15, somewhat circular in cross-section, is worked in, whose depth decreases its ends. At the turning position of the tightening-ring 8 as shown in FIG. 2 to 5 and 7, a clamp ball bearing 11 is found, in such position pressed in the cavity 14, that is, anterior sleeve 2 and grip sleeve 3 are locked together. If, however, the tightening-ring 8—as shown in the drawings in FIGS. 3, 5 and 7—is turned counter-clockwise, then the clamp ball bearing 11 arrives in the indentation 15 and thereby outside the grip with the cavity 14, so that anterior sleeve 2 and grip sleeve 3 can be pulled apart from each other. In this way tightening-ring 8 effects a non-turning detachable linkage between the anterior and grip sleeves.

On the dental-instrument handle as shown in FIG. 1 the forward part of the grip sleeve 3 is bent, and the handle head 7 is also bent. It is possible, that both bends be left out, and a straight dental-instrument handle be made in this way.

The handle sleeve 1 is provided with a coolant line 16 running along the area of its transverse space in the inside of the sleeve outside of its longitudinal axis (A), which is divided transversely at said space and leads to the area of the dental-instrument drill 6. The coolant line 16 is attached to an adjusting screw 16b provided on the connecting sleeve 4.

Of the both front sides—facing one another of the anterior sleeve 2 and the grip sleeve 3, the one front side is provided with a protruding connecting piece 17 of the coolant line 16 and/or with a connecting socket 18 for the insertable connecting piece 17. The front sides—both facing one another—are further provided with flexible catch means 20 and—with respect to the axis A of the handle—axially engagable in opposing catch means 19. Therefore, the catch means 20 are on one of the front sides and the opposing catch means 19 are on the other front side. The catch means 20 as well as the opposing catch means 19 are laid out in an axial direction. In the examples as shown in FIG. 3 and 7 many catch means 20 as well as opposing catch means as well as opposing catch means 19 are arranged, wherein the catch means as well as the opposing catch means are arranged symmetrically on a circular path. In the examples as shown in FIGS. 3 and 5 there are two catch means 20 and/or opposing catch means 19, in examples as shown in FIG. 7 six catch means 20 and/or opposing catch means 19 are provided.

The connecting piece 17 and/or the connecting socket 18 of the coolant line(s) 16 are also arranged on the circular path of the catch means 20 and the opposing catch means 19, especially as shown in FIGS. 5 and 7. As FIGS. 3, 5 and 7 show, two coolant lines 16 are provided according to the representations, wherein the one serves for cool water and the other for cool air.

In the example shown in FIGS. 7, the connecting pieces 17 and the connecting sockets 18 of the coolant lines 16 are arranged symmetrically on said circular path together with the catch means 20 and/or opposing catch means 19.

FIG. 8 shows for the sake of completeness the carrier gearwheel of the drive shaft that is mounted in anterior sleeve 2 and that is not illustrated.

The coolant lines 16 as well as the catch means 20 and opposing catch means 19 are provided in the wall of the anterior sleeve 2 and at least partly in the wall of the grip sleeve. Therefore, the coolant lines 16 that are found in the grip sleeve 3 run in special receiver canals 16a whereby it is made possible, that the coolant lines 16, made like a hose, can be easily taken apart after separation of both sleeves 2, 3 for the purpose of cleaning or replacement. As shown in FIGS. 2, 4 and 6, the receiver canal 16a is worked in one part of the length of grip sleeve 3 from the outside into the wall of the sleeve and covered by the tightening-ring 8 which surrounds the sleeve 3. The portion of the coolant line found in anterior sleeve 2 is made as the cylinder provided in the wall of the sleeve.

In the examples as shown in FIGS. 2 and 3, for the formation of the catch means 20 the one front side is provided with two groups of clamping jaws arranged next to one another, left alone as one slot effecting the flexible gripping, and for the formation of the opposing catch means 19 the other front side is provided with one recess that receives together all clamping jaws of a group. Thereby, the said receivers are made by slots from the frontal border of the grip sleeve 3, while the clamping jaws making the catch means 20 are created as projections leading from the frontal border of the anterior sleeve 2.

In the examples shown in FIGS. 4 to 7, for formation of the catch means 20 the one front side is provided with at least one guide pin and for formation of the opposing catch means the other front side is provided with the guide pin(s) attached and for receiving the last working plug sockets, that has, in its inside on the guide pin, elastic middles 22 as a supplement for the flexible gripping. The elastic middles 22 are made by a sleeve arranged in the plug socket out of elastic material. A rigid guide sleeve 23, in the direction of insertion before the elastic middles 22, is arranged for the guide pin. The guide sleeve 23 can be made of metal or plastic.

The connecting sockets 18 of the coolant lines 16 as well as the plug sockets are provided with elastic middles 24 in the insides as a supplement on the insertable connecting pieces 17. In this case also, the elastic middles 24 are made by a sleeve out of elastic material arranged in the connecting socket 18, wherein a rigid guide sleeve 25 is arranged for the connecting pieces 17 in the direction of insertion before the elastic middles 24. Then the rigid guide sleeve 25 can be made of metal or plastic in this case.

The elastic centers 22, 24 have a Shore-hardness of 70 to 80°.

In the example shown in FIG. 7 the guide pins making the catch means 20 as well as the connecting pieces 17 of the coolant lines 16 are arranged symmetrically on the circular path on the front side of the grip sleeve 3 and the plug sockets making the opposing catch means 19 as well as the connecting sockets 18 of coolant lines 16 are arranged symmetrically with the same diameter as the first-mentioned circular path on the front side of the anterior sleeve 2. The plug sockets making the opposing catch means 19 are connected over a cut-off canal 26a with a belt canal, from there the coolant line portion 16 of the anterior sleeve 2 leads to the area of the dental-treatment drill 6. Seals 27 are also attached to the belt canal. This embodiment of the invention makes it possible, that the anterior sleeve 2 and the grip sleeve 3 can be connected to one another in various opposing turning positions.

I claim

1. Dental handpiece comprising an elongated handle sleeve transversely divided by formation of an anterior sleeve showing a receptable for a drivable dental treatment instrument and a connected grip sleeve detachable by means of a rotatable tightening ring; said handle sleeve having a coolant line running at least in the area of the transverse space within the inside of the sleeve outside the longitudinal axis of the handle sleeve, said coolant line also being transversely divided and leading to the area of the dental-treatment instrument; and anterior sleeve and the grip sleeve having both two front sides facing each other, one front side being provided with a projecting connecting piece for the cooling line and the other front side being provided with a connecting socket for an insertable connecting piece; the front side of the grip sleeve being provided with guide pins projecting from it and forming catch means opposing pin sockets of elastic material and serving as opposing catch means to accept the guide pins and being admitted into the front end of the anterior sleeve, a connecting socket for the connecting piece of each coolant line also being comprised of elastic material, said guide pins as well as the connecting pieces of each coolant line being mounted at equal intervals along a circular path on the front side of the grip sleeve, said pin sockets and the connecting socket of each coolant line being mounted at equal intervals along a circular path with the same diameter as the previously mentioned circular path on the front side of the anterior sleeve, the connecting pieces of each coolant line being connected with a belt canal from which the cooling line portion of the anterior sleeve leads to the area of the dental-treatment instrument.

2. Dental-instrument handle, according to claim 1, characterized in that, the elastic material (22, 24) has a Shore-hardness of 70°–80°.

3. Dental-instrument handle, according to claim 1, characterized in that, at least the coolant line portion (16) of the grip sleeve has a hose arranged as in one in the receiver canal (16a) provided in the wall of the sleeve.

4. Dental-instrument handle, according to claim 3, characterized in that, the receiver canal (16a) is worked in at least at one part of the length with the sleeve from the outer side into the wall of the sleeve and is covered by the tightening-ring (8) that surrounds the sleeve.

5. Dental-instrument handle, according to claim 4, characterized in that, at least the coolant line portion (16) of the anterior sleeve (2) has a cylinder provided in the wall of the sleeve.

* * * * *